(12) United States Patent
Burns et al.

(10) Patent No.: US 7,834,031 B2
(45) Date of Patent: Nov. 16, 2010

(54) RADIOLABELED GLYCINE TRANSPORTER INHIBITORS

(75) Inventors: H. Donald Burns, Harlysville, PA (US); Terence G. Hamill, Landsdale, PA (US); Craig W. Lindsley, Brentwood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 406 days.

(21) Appl. No.: 11/991,727

(22) PCT Filed: Sep. 25, 2006

(86) PCT No.: PCT/US2006/036989

§ 371 (c)(1),
(2), (4) Date: Mar. 5, 2008

(87) PCT Pub. No.: WO2007/041025

PCT Pub. Date: Apr. 12, 2007

(65) Prior Publication Data
US 2009/0269278 A1    Oct. 29, 2009

Related U.S. Application Data

(60) Provisional application No. 60/721,782, filed on Sep. 29, 2005.

(51) Int. Cl.
*A61K 31/445* (2006.01)
*C07D 211/06* (2006.01)
*C07D 401/04* (2006.01)

(52) U.S. Cl. ............... 514/318; 546/184; 546/192; 546/207; 546/208; 514/315

(58) Field of Classification Search ............ 546/184, 546/192, 207, 208; 514/315, 318
See application file for complete search history.

(56) References Cited

U.S. PATENT DOCUMENTS

| | | | |
|---|---|---|---|
| 4,931,270 A | 6/1990 | Horn et al. | |
| 6,241,964 B1 * | 6/2001 | Burns et al. | 424/1.89 |
| 6,303,637 B1 * | 10/2001 | Bao et al. | 514/331 |
| 6,458,935 B1 * | 10/2002 | Burns et al. | 534/10 |
| 6,939,966 B2 * | 9/2005 | Burns et al. | 544/331 |
| 7,354,935 B2 * | 4/2008 | Burns et al. | 514/326 |
| 2007/0105902 A1 | 5/2007 | Lindsley et al. | |
| 2007/0254880 A1 | 11/2007 | Blackaby et al. | |

FOREIGN PATENT DOCUMENTS

WO    WO 2005/046601    5/2005
WO    2005/094514 A2    10/2005

* cited by examiner

*Primary Examiner*—Golam M Shameem
(74) *Attorney, Agent, or Firm*—Geened Devlin; Raynard Yuro

(57) ABSTRACT

The present invention is directed to radiolabeled glycine transporter inhibitors which are useful for the labeling and diagnostic imaging of glycine transporters in mammals.

14 Claims, No Drawings

RADIOLABELED GLYCINE TRANSPORTER INHIBITORS

CROSS REFERENCE TO RELATED APPLICATIONS

This application is a U.S. National Phase application under 35 U.S.C. §371 of PCT Application No. PCT/US2006/036989, filed Sep. 25, 2006, which claims priority under 35 U.S.C. §119 from U.S. Application No. 60/721,782, filed Sep. 29, 2005.

BACKGROUND OF THE INVENTION

Noninvasive, nuclear imaging techniques can be used to obtain basic and diagnostic information about the physiology and biochemistry of a variety of living subjects including experimental animals, normal humans and patients. These techniques rely on the use of sophisticated imaging instrumentation that is capable of detecting radiation emitted from radiotracers administered to such living subjects. The information obtained can be reconstructed to provide planar and tomographic images that reveal distribution of the radiotracer as a function of time. Use of appropriately designed radiotracers can result in images which contain information on the structure, function and most importantly, the physiology and biochemistry of the subject. Much of this information cannot be obtained by other means. The radiotracers used in these studies are designed to have defined behaviors in vivo which permit the determination of specific information concerning the physiology or biochemistry of the subject or the effects that various diseases or drugs have on the physiology or biochemistry of the subject. Currently, radiotracers are available for obtaining useful information concerning such things as cardiac function, myocardial blood flow, lung perfusion, liver function, brain blood flow, regional brain glucose and oxygen metabolism.

Compounds can be labeled with either positron or gamma emitting radionuclides. For imaging, the most commonly used positron emitting (PET) radionuclides are $^{11}C$, $^{18}F$, $^{15}O$ and $^{13}N$, all of which are accelerator produced, and have half lives of 20, 110, 2 and 10 minutes, respectively. Since the half-lives of these radionuclides are so short, it is only feasible to use them at institutions that have an accelerator on site or very close by for their production, thus limiting their use. Several gamma emitting radiotracers are available which can be used by essentially any hospital in the U.S. and in most hospitals worldwide. The most widely used of these are $^{99m}Tc$, $^{201}Tl$ and $^{123}I$.

In the last two decades, one of the most active areas of nuclear medicine research has been the development of receptor imaging radiotracers. These tracers bind with high affinity and specificity to selective receptors and neuroreceptors. Successful examples include radiotracers for imaging the following receptor systems: estrogen, muscarinic, dopamine D1 and D2, opiate, neuropeptide-Y, cannabinoid-1 and neurokinin-1.

The NMDA receptor plays a critical role in a variety of neurophysiological phenomena, including but not limited to synaptic plasticity, cognition, attention and memory (Bliss T and Collingridge W, 1993, Nature 361:31; Morris R G M et al., 1986, Nature 319:774). Psychotomimetic drugs constitute a wide class of drugs including psychomotor stimulants (cocaine, amphetamine), hallucinogens (LSD), and NMDA receptor antagonists (PCP, ketamine). Of these, only the NMDA receptor antagonists appear to elicit a robust induction of the positive, negative, and cognitive symptoms of schizophrenia. Besides schizophrenia, dysfunction of glutamatergic pathways has been implicated in a number of disease states in the human central nervous system (CNS) including but not limited to cognitive deficits, dementia, Parkinson disease, Alzheimer disease and bipolar disorder. NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses. Clinical trials in which high doses of glycine were administered orally as an add-on to standard neuroleptic therapy showed an improvement of the symptoms of schizophrenia patients (Javitt et al. Int. J. Neuropsychopharmacol. (2001) 4: 385-391). One way to increase synaptic glycine levels without administering exogenous glycine is to inhibit its removal from the synapse. Evidence that this approach would be useful in treating schizophrenia comes from a double-blind placebo controlled study in which sarcosine was administered to patients suffering from schizophrenia, but who were poorly responsive to antipsychotic drugs. A beneficial effect was observed on positive, negative and cognitive symptoms, indicating that inhibition of glycine re-uptake is a reasonable approach to the treatment of schizophrenia.

Two specific glycine transporters, GlyT1 and GlyT2 have been identified and shown to belong to the $Na^+/Cl^-$ dependent family of neurotransmitter transporters which includes taurine, γ-aminobutyric acid (GABA), proline, monoamines and orphan transporters (Smith K E et al., 1992, Neuron 8:927; Borowsky B et al., 1993, Neuron 10:851; Liu Q R et al., 1993, J. Biol. Chem. 268:22802; Kim K M et al., 1994, Mol. Pharmacol. 45:608; Morrow J A et al., 1998, FEBS Lett. 439:334; Nelson N, 1998, J. Neurochem. 71:1785). GlyT1 and GlyT2 have been isolated from different species and shown to have only 50% identity at the amino acid level. They also have a different pattern of expression in mammalian central nervous system with GlyT2 being expressed in spinal cord, brainstem and cerebellum and GlyT1 present in these regions as well as forebrain areas such as cortex, hippocampus, septum and thalamus (Smith K E et al., 1992, Neuron 8:927; Borowsky B et al., 1993, Neuron 10:851; Liu Q R et al., 1993, J. Biol. Chem. 268:22802). At the cellular level, GlyT2 has been reported to be expressed by glycinergic nerve endings in rat spinal cord whereas GlyT1 appears to be preferentially expressed by glial cells (Zafra F et al., 1995, J. Neurosci. 15:3952). These expression studies have led to the conclusion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])sarcosine (NFPS) potentiates NMDA receptor activity and NMDA receptor-dependent long-term potentiation in rat (Bergeron R et al., 1998, PNAS USA 95:15730; Kinney G et al., 2003, J. Neurosci. 23:7586). Furthermore, NFPS has been reported to enhance pre-pulse inhibition in mice, a measure of sensory gating that is known to be deficient in schizophrenia patients (Kinney G et al., 2003, J. Neurosci. 23:7586). These physiological effects of GlyT1 in forebrain regions together with clinical reports showing the beneficial effects of GlyT1 inhibitor sarcosine in improving symptoms in schizophrenia patients (Tsai and Coyle WO99/52519) indicate that selective GlyT1 uptake inhibitors represent a new class of antipsychotic drugs.

PET (Positron Emission Tomography) radiotracers and imaging technology may provide a powerful method for clinical evaluation and dose selection of glycine transporter GlyT1 inhibitors. Using a fluorine-18 or carbon-11 labeled radiotracer that provides a glycine transporter GlyT1-specific image in the brain and other tissues, the dose required to saturate glycine transporter GlyT1 can be determined by the blockade of the PET radiotracer image in humans. The rationale for this approach is as follows: efficacy of a glycine transporter GlyT1 inhibitor is a consequence of the extent of transporter inhibition, which in turn is a function of the degree of drug-transporter occupancy. Certain radiolabeled ligands of the glycine transporter are described by Ravert et al., Journal of Labelled Compounds and Radiopharmaceuticals, 44, 241-246 (2001).

It is, therefore, an object of this invention to develop radiolabeled glycine transporter GlyT1 inhibitors that would be useful not only in traditional exploratory and diagnostic imaging applications, but would also be useful in assays, both in vitro and in vivo, for labeling the glycine transporter GlyT1 and for competing with unlabeled glycine transporter GlyT1 inhibitors. It is a further object of this invention to develop novel assays which comprise such radiolabeled compounds. It is yet a further object of the present invention to develop intermediates for the synthesis of radiolabled glycine transporter GlyT1 inhibitors.

SUMMARY OF THE INVENTION

The present invention is directed to certain radiolabeled glycine transporter inhibitors, in particular radiolabeled GlyT1 glycine transporter inhibitors. The present invention is further concerned with methods for the use of such radiolabeled radiolabeled glycine transporter inhibitors for the labeling and diagnostic imaging of glycine transporters, including GlyT1 glycine transporters, in mammals. Still further, the present invention is directed to intermediates useful for the synthesis of radiolabeled radiolabeled glycine transporter inhibitors. The invention is also concerned with pharmaceutical formulations comprising one of the compounds as an active ingredient. The invention is further concerned with processes for preparing the compounds of this invention.

DETAILED DESCRIPTION OF THE INVENTION

The present invention is directed to compounds of the formula I:

I wherein:

A is selected from N and CH;

$R^{2a}$ and $R^{2b}$ are independently selected from the group consisting of:
(1) hydrogen,
(2) fluoro,
(3) chloro, and
(4) bromo;

$R^3$ is $C_{1-6}$alkyl, which is unsubstituted or substituted with fluoro;

$R^4$ is selected from the group consisting of:
(1) hydrogen, and
(2) $C_{1-3}$alkyl;

one of X and Y is selected from the group consisting of:
(1) $^{18}F$,
(2) —O($^{11}CH_3$), and
(3) —O($CD_2{}^{18}F$),
and the other of X and Y is hydrogen;

or a pharmaceutically acceptable salt thereof or an individual enantiomer or diastereomer thereof.

An embodiment of the present invention includes compounds of the formula Ia:

Ia wherein $R^4$ is $C_{1-3}$alkyl, and A, $R^{2a}$, $R^{2b}$, $R^3$, X and Y are defined herein;

or a pharmaceutically acceptable salt thereof.

An embodiment of the present invention includes compounds wherein A is N of the formula Ib:

Ib wherein $R^{2a}$, $R^{2b}$, $R^3$, $R^4$, X and Y are defined herein;

or a pharmaceutically acceptable salt thereof.

Another embodiment of the present invention includes compounds wherein A is CH.

An embodiment of the present invention includes compounds wherein $R^{2a}$ and $R^{2b}$ are independently selected from the group consisting of:

(1) hydrogen,
(2) fluoro, and
(3) chloro.

Within this embodiment, the present invention includes compounds wherein $R^{2a}$ is chloro and $R^{2b}$ is chloro. Also within this embodiment, the present invention includes compounds wherein $R^{2a}$ is chloro and $R^{2b}$ is hydrogen. Also within this embodiment, the present invention includes compounds wherein $R^{2a}$ is fluoro and $R^{2b}$ is hydrogen.

An embodiment of the present invention includes compounds wherein $R^3$ is —$CH_2CH_3$. Another embodiment of the present invention includes compounds wherein $R^3$ is —$(CH_2)_2CH_3$.

An embodiment of the present invention includes compounds wherein $R^4$ is methyl. Within this embodiment, the present invention includes compounds wherein $R^4$ is methyl in the (S) configuration.

An embodiment of the present invention includes compounds wherein X is $^{18}F$ and Y is hydrogen. Another embodiment of the present invention includes compounds wherein X is hydrogen and Y is $^{18}F$. Another embodiment of the present invention includes compounds wherein X is —$O(^{11}CH_3)$ and Y is hydrogen. Another embodiment of the present invention includes compounds wherein X is hydrogen and Y is —$O(CD_2{}^{18}F)$.

Specific embodiments of the present invention include a compound which is selected from the group consisting of the subject compounds of the Examples herein and pharmaceutically acceptable salts thereof and individual enantiomers and diastereomers thereof.

The compounds of the present invention may contain one or more chiral centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-3}$, as in $C_{1-3}$alkyl is defined to identify the group as having 1, 2 or 3 carbons in a linear or branched arrangement, such that $C_{1-3}$alkyl specifically includes methyl, ethyl, n-propyl, and iso-propyl. A group which is designated as being independently substituted with substituents may be independently substituted with multiple numbers of such substituents.

As appreciated by those of skill in the art, "D" or deutero as used herein are intended to include the isotope $^2H$ or deuterium.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

The present invention is also directed to a method for labeling GlyT1 glycine transporters in a mammal which comprises administering to a mammal in need of such labeling an effective amount of the radiolabeled compound of the present invention.

The present invention is also directed to a method for diagnostic imaging of GlyT1 glycine transporters in a mammal which comprises administering to a mammal in need of such diagnostic imaging an effective amount of the radiolabeled compound of the present invention.

The present invention is also directed to a method for diagnostic imaging of tissues bearing GlyT1 glycine transporters in a mammal which comprises administering to a mammal in need of such diagnostic imaging an effective amount of the radiolabeled compound of the present invention.

The present invention is also directed to a method for the diagnostic imaging of GlyT1 glycine transporters in tissues of a mammalian species which comprises administering to the mammalian species in need of such diagnostic imaging an effective amount of the radiolabeled compound of the present invention.

The present invention is also directed to a method for diagnostic imaging of the brain in a mammal which comprises administering to a mammal in need of such diagnostic imaging an effective amount of the radiolabeled compound of the present invention.

The present invention is further directed to a method for the detection or quantification of GlyT1 glycine transporters in mammalian tissue which comprises administering to a mammal in which such quantification is desired an effective amount of the radiolabeled compound of the present invention.

In a preferred embodiment of the methods of the present invention, the mammal is a human.

Suitable radionuclides that may be incorporated in the instant compounds include $^3H$ (also written as T), $^{11}C$, $^{18}F$, $^{125}I$, $^{82}Br$, $^{123}I$, $^{131}I$, $^{75}Br$, $^{15}O$, $^{13}N$, $^{211}At$ or $^{77}Br$. The radionuclide that is incorporated in the instant radiolabeled compounds will depend on the specific analytical or pharmaceutical application of that radiolabeled compound. Thus, for in vitro labeling of GlyT1 glycine transporters and competition assays, compounds that incorporate $^3H$, $^{125}I$ or $^{82}Br$ will generally be most useful. For diagnostic imaging agents, compounds that incorporate a radionuclide selected from $^{11}C$, $^{18}F$, $^{123}I$, $^{131}I$, $^{75}Br$, $^{76}Br$ or $^{77}Br$ are preferred. In certain applications incorporation of a chelating radionuclide such as $Tc^{99m}$ may also be useful. $^{18}F$ may be preferable over $^{11}C$ because with the longer half-life of $^{18}F$, imaging can be carried out long enough to allow a more specific signal to develop and improved conditions for receptor quantification studies.

Radiolabeled glycine transporter GlyT1 inhibitors, when labeled with the appropriate radionuclide, are potentially useful for diagnostic imaging, basic research, and radiotherapeutic applications. Specific examples of possible diagnostic imaging and radiotherapeutic applications, include determining the location, the relative activity and/or the abundance of GlyT1 glycine transporters, radioimmunoassay of glycine transporter GlyT1 inhibitors, and autoradiography to determine the distribution of GlyT1 glycine transporters in a mammal or an organ or tissue sample thereof.

In particular, the instant radiolabeled glycine transporter GlyT1 inhibitors when labeled with the positron emitting radionuclide, F-18, are useful for positron emission tomographic (PET) imaging of GlyT1 glycine transporters in the brain of living humans and experimental animals. These radiolabeled glycine transporter GlyT1 inhibitors may be used as research tools to study the interaction of unlabeled GlyT1 glycine transporter inhibitors with GlyT1 glycine transporters in vivo via competition between the labeled drug and the radiolabeled compound for binding to the receptor. These types of studies are useful for determining the relationship between GlyT1 glycine transporter occupancy and dose of unlabeled glycine transporter GlyT1 inhibitor, as well as for studying the duration of blockade of the receptor by various doses of the unlabeled glycine transporter GlyT1 antagonist, agonists, and inverse agonists. As a clinical tool, the radiolabeled glycine transporter GlyT1 inhibitors may be used to help define a clinically efficacious dose of a glycine transporter GlyT1 inhibitor. In animal experiments, the radiolabeled glycine transporter GlyT1 inhibitors can be used to provide information that is useful for choosing between potential drug candidate for selection for clinical development. The radiolabeled glycine transporter GlyT1 inhibitors may also be used to study the regional distribution and concentration of GlyT1 glycine transporters in the living human brain, as well as the brain of living experimental animals and in tissue samples. The radiolabeled glycine transporter GlyT1 inhibitors may also be used to study disease or pharmacologically related changes in GlyT1 glycine transporter concentrations.

For example, positron emission tomography (PET) tracer such as the present radiolabeled glycine transporter GlyT1 inhibitors which can be used with currently available PET technology to obtain the following information: relationship between level of receptor occupancy by candidate glycine transporter GlyT1 inhibitors and clinical efficacy in patients; dose selection for clinical trials of glycine transporter GlyT1 inhibitors prior to initiation of long term clinical studies; comparative potencies of structurally novel glycine transporter GlyT1 inhibitors; investigating the influence of glycine transporter GlyT1 inhibitors on in vivo transporter affinity and density during the treatment of clinical targets with glycine transporter GlyT1 inhibitors and other agents; changes in the density and distribution of GlyT1 glycine transporters during e.g. psychiatric diseases in their active stages, during effective and ineffective treatment and during remission; and changes in glycine transporter GlyT1 expression and distribution in CNS disorders; imaging neurodegenerative disease where GlyT1 glycine transporters are upregulated; imaging neurodegenerative disease where GlyT1 glycine transporters are involved; and the like.

The NMDA receptor is central to a wide range of CNS processes, and plays a role in a variety of disease states in humans or other species. The action of GlyT1 transporters affects the local concentration of glycine around NMDA receptors. Selective GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Because a certain amount of glycine is needed for the efficient functioning of NMDA receptors, any change to that local concentration can affect NMDA-mediated neurotransmission. Changes in NMDA-mediated neurotransmission have been implicated in certain neuropsychiatric disorders such as dementia, depression and psychoses, for example schizophrenia, and learning and memory disorders, for example attention deficit disorders and autism.

The radiolabeled glycine transporter inhibitors of the present invention have utility in imaging glycine transporters or for diagnostic imaging with respect to a variety of neurological and psychiatric disorders associated with glutamatergic neurotransmission dysfunction, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

Of the disorders above, the radiolabeled glycine transporter inhibitors of the present invention are of particular importance in imaging glycine transporters with respect to schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss.

For the use of the instant compounds as exploratory or diagnostic imaging agents the radiolabeled compounds may be administered to mammals, preferably humans, in a pharmaceutical composition, either alone or, preferably, in combination with pharmaceutically acceptable carriers or diluents, optionally with known adjuvants, such as alum, in a pharmaceutical composition, according to standard pharmaceutical practice. Such compositions can be administered orally or parenterally, including the intravenous, intramuscular, intraperitoneal, subcutaneous, rectal and topical routes of administration. Preferably, administration is intravenous. Radiotracers labeled with short-lived, positron emitting radionuclides are generally administered via intravenous injection within less than one hour of their synthesis. This is necessary because of the short half-life of the radionuclides involved (20 and 110 minutes for C-11 and F-18 respectively).

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof. The terms "administration of" and or "administering a" compound should be understood to mean providing a compound of the invention or a prodrug of a compound of the invention to the patient.

The pharmaceutical compositions of this invention may be used in the form of a pharmaceutical preparation, for example, in solid, semisolid or liquid form, which contains one or more of the compound of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

An appropriate dosage level for the unlabeled glycine transporter GlyT1 inhibitor will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

When a radiolabeled glycine transporter GlyT1 inhibitor according to this invention is administered into a human subject, the amount required for diagnostic imaging will normally be determined by the prescribing physician with the dosage generally varying according to the age, weight, and response of the individual patient, as well as the quantity of emission from the radionuclide. However, in most instances, an effective amount will be the amount of compound sufficient to produce emissions in the range of from about 1-5 mCi.

In one exemplary application, administration occurs in an amount of radiolabeled compound of between about 0.005 μg/kg of body weight to about 50 μg/kg of body weight per day, preferably of between 0.02 μg/kg of body weight to about 3 μg/kg of body weight. A particular analytical dosage that comprises the instant composition includes from about 0.5 μg to about 100 μg of a labeled glycine transporter GlyT1 inhibitor. Preferably, the dosage comprises from about 1 μg to about 50 μg of a radiolabeled glycine transporter GlyT1 inhibitor.

The following illustrative procedure may be utilized when performing PET imaging studies on patients in the clinic. The patient is premedicated with unlabeled glycine transporter GlyT1 inhibitor (at doses 300, 100, or 30 mg/day) for 2 weeks prior to the day of the experiment and is fasted for at least 12 hours allowing water intake ad libitum. A 20 G two inch venous catheter is inserted into the contralateral ulnar vein for radiotracer administration.

The patient is positioned in the PET camera and a tracer dose of $[^{15}O]H_2O$ administered via i.v. catheter. The image thus obtained is used to insure that the patient is positioned correctly to include the brain or other areas of interest. Subsequently the $[^{18}F]$ glycine transporter GlyT1 inhibitor (<20 mCi) is administered via i.v. catheter. Following the acquisition of the total radiotracer image, an infusion is begun of the glycine transporter GlyT1 inhibitor which is being clinically evaluated at one of three dose rates (0.1, 1 or 10 mpk/day). After infusion for 2.5 hrs, the $[^{18}F]$ glycine transporter GlyT1 inhibitor is again injected via the catheter. Images are again acquired for up to 90 min. Within ten minutes of the injection of radiotracer and at the end of the imaging session, 1 ml blood samples are obtained for determining the plasma concentration of the clinical candidate.

For determining the distribution of radiotracer, regions of interest (ROIs) are drawn on the reconstructed image including, e.g. the brain and the central nervous system. These regions are used to generate time activity curves obtained in the absence of receptor antagonist or in the presence of the clinical candidate at the various infusion doses examined. Data are expressed as radioactivity per unit time per unit volume (μCi/cc/mCi injected dose). Inhibition curves are generated from the data obtained in a region of interest obtained starting at 70 minutes post-injection of radiotracer. At this time, clearance of non-specific binding has reached steady state. The $ID_{50}$ values are obtained by curve fitting the dose-rate/inhibition curves with equation iii:

$$B=A_0-A_0*I/(ID_{50}+I)+NS \qquad \text{(iii)}$$

where B is the %-Dose/g of radiotracer in tissues for each dose of clinical candidate, $A_0$ is the specifically bound radiotracer in a tissue in the absence of a glycine transporter GlyT1 inhibitor, I is the injected dose of antagonist, $ID_{50}$ is the dose of compound which inhibits 50% of specific radiotracer binding to a glycine transporter GlyT1, and NS is the amount of non-specifically bond radiotracer.

Gamma Camera Imaging

Two rats are anesthetized (ketamine/ace-promazine), positioned on the camera head, and their tail veins canulated for ease of injection. One rat is preinjected with an unlabeled glycine transporter GlyT1 inhibitor (10% EtOH/27% PEG/63% $H_2O$) 30 min. prior to injection of radiotracer to demonstrate non-specific binding. 150 uCi/rat of an $^{18}F$ labeled glycine transporter GlyT1 inhibitor is injected via its tail vein, and the catheters flushed with several mls of normal saline. Acquisition of images is started as the radiotracer was injected. Sixty, one minute images are acquired and the rats are subsequently euthanized with sodium pentobarbital. Regions of interest (ROIs) are drawn on the first image which includes the brain, then used to analyze the count rates in subsequent images. ROIs are defined to remain fairly clear during the course of the study, and are assumed to be representative of the entire organ. Count-rates are converted to %-dose/ROI by dividing the count-rate in the ROI by that of the whole rat, which is then multiplied by 100.

PET Imaging in Dogs

Female beagle dogs weighing 7.7-14.6 kg (11.0±2.3 kg) are premedicated with unlabeled glycine transporter GlyT1 inhibitor (at doses 300, 100, or 30 mg/day) for 2 weeks prior to the day of the experiment and are fasted for at least 12 hours allowing water intake ad libitum. A 20 G two inch venous catheter is placed into the right front leg ulnar vein through which anesthesia is introduced by sodium pentobarbital 25-30 mg/kg in 3-4 ml and maintained with additional pentobarbital at an average dose of 3 mg/kg/hr. Another catheter is inserted into the contralateral ulnar vein for radiotracer administration.

Oxygen saturation of circulating blood is measured with a pulse oximeter (Nellcor Inc., Hayward, Calif.) placed on the tongue of the animal. Circulatory volume is maintained by intravenous infusion of isotonic saline. A 22 G cannula is inserted into the anterior tibial or distal femoral artery for continuous pressure monitoring (Spacelabs™, model 90603A). EKG, heart rate, and core temperature are monitored continuously. In particular, EKG is observed for ST segment changes and arrhythmias.

The animal is positioned in the PET camera and a tracer dose of $[^{15}O]H_2O$ administered via i.v. catheter. The image thus obtained is used to insure that the dog is positioned correctly to include the brain and other areas of interest. Subsequently $[^{18}F]$-glycine transporter GlyT1 inhibitor (<20 mCi) is administered via i.v. catheter. Following the acquisition of the total radiotracer image, an infusion is begun of the unlabeled glycine transporter GlyT1 inhibitor at one of three dose rates (0.1, 1 or 10 mpk/day). After infusion for 2.5 hrs, $[^{18}F]$-glycine transporter GlyT1 inhibitor is again injected via the catheter. Images are again acquired for up to 90 min. Within ten minutes of the injection of radiotracer and at the end of the imaging session, 1 ml blood samples are obtained for determining the plasma concentration of test compound. In one imaging session, a dose of 10 mpk another glycine transporter GlyT1 inhibitor is infused over 5 minutes. This dose has been determined to completely block radiotracer binding and thus is used to determine the maximum receptor-specific signal obtained with the PET radiotracer. At the conclusion of the study, animals are recovered and returned to animal housing.

For uninhibited distribution of radiotracer, regions of interest (ROIs) are drawn on the reconstructed image including the brain. These regions are used to generate time activity curves obtained in the absence of test compound or in the presence of test compound at the various infusion doses examined. Data are expressed as radioactivity per unit time per unit volume (μCi/cc/mCi injected dose). Inhibition curves are generated from the data obtained in a region of interest obtained starting at 70 min. post-injection of radiotracer. By this time, clearance of non-specific binding will have reached steady state. The $ID_{50}$ are were obtained by curve fitting the dose-rate/inhibition curves with equation iii, hereinabove.

The utility of the compounds of the present invention in inhibiting the glycine transporter activity, in particular GlyT1 activity, may be demonstrated by methodology known in the art. Human placental choriocarcinoma cells (JAR cells (ATCC No. HTB-144)) endogenously expressing GlyT1 were cultured in 96-well Cytostar scintillating microplates (Amersham Biosciences) in RPMI 1640 medium containing 10% fetal calf serum in the presence of penicillin (100 micrograms/milliliter) and streptomycin (100 micrograms/milliliter). Cells were grown at 37° C. in a humidified atmosphere of 5% CO2 for 40-48 hours before the assay. Culture medium was removed from the Cytostar plate, and JAR cells were incubated with 30 microliters of TB1A buffer (120 mM NaCl, 2 mM KCl, 1 mM $CaCl_2$, 1 mM $MgCl_2$, 10 mM HEPES, 5 mM L-alanine, pH 7.5 adjusted with Tris base) with or without the compounds of the present invention for 1 minute. Then 30 microliters of $[^{14}C]$-glycine diluted with TB1A was added to each well to give a final concentration of 10 micromolar. After incubation at room temperature for 3 hours, the Cytostar scintillating microplates were sealed and counted on a Top Count scintillation counter (Packard). Non-specific uptake of $[^{14}C]$-glycine was determined in the presence of 10 mM unlabeled glycine. $[^{14}C]$taurine uptake experiments were performed according to the same protocol except that 10 mM unlabeled taurine was used to determine non-specific uptake. To determine potencies, a range of concentrations of the compounds of the present invention was added to the cells, followed by the fixed concentration of $[^{14}C]$glycine. The concentration of the present compound that inhibited half of the specific uptake of $[^{14}C]$glycine ($IC_{50}$ value) was determined from the assay data by non-linear curve fitting. In particular, the compounds of the following examples had activity in inhibiting specific uptake of $[^{14}C]$glycine in the aforementioned assay, generally with an $IC_{50}$ value of less than about 10 micromolar. Preferred compounds within the present invention had activity in inhibiting specific uptake of $[^{14}C]$glycine in the aforementioned assay with an $IC_{50}$ value of less than about 1 micromolar. These compounds were selective for $[^{14}C]$glycine uptake (by GlyT1 in the JAR cells) compared to $[^{14}C]$taurine uptake (by the taurine transporter TauT in the JAR cells). Such a result is indicative of the intrinsic activity of the compounds as inhibitors of GlyT1 transporter activity.

The present invention is further directed to a method for the diagnostic imaging of glycine transporter GlyT1 in a mammal in need thereof which comprises combining a compound of the present invention with a pharmaceutical carrier or excipient.

Abbreviations used in the description of the chemistry and in the Examples that follow are: $CH_2Cl_2$ dichloromethane; DIEA diisopropylethylamine; PS-DIEA polystyrene diisopropylethylamine; PS-DMAP polystyrene 4-N,N-dimethylaminopyridine; DCC dicyclohexylcarbodiimide; Ra—Ni Raney Nickel; HOBt hydroxybenzotriazole; THF tetrahydrofuran; TFA trifluoroacteic acid; MeOH methanol.

Several methods for preparing the compounds of this invention are illustrated in the following Schemes and Examples. Starting materials and the requisite intermediates are in some cases commercially available, or can be prepared according to literature procedures or as illustrated herein.

The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures.

Glycine transporter inhibitors which incorporate a radionuclide may be prepared by first synthesizing an unlabeled compound that optionally incorporates a iodo or bromo moiety and then exchanging a hydrogen or halogen moiety with an appropriate radionuclide using techniques well known in the art. Alternately, a radiolabeled glycine transporter inhibitor may be prepared by alkylation with a radiolabeled alkylating agent. Syntheses of particular glycine transporter inhibitors are described below. During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art. In particular, amino moieties may be protected by, for example, the formation of alkoxycarbonyl derivatives, e.g. tert-butoxycarbonyl and trichloroethoxycarbonyl, or benzyl, trityl or benzyloxycarbonyl derivatives. Subsequent removal of the protecting group is achieved by conventional procedures thus, for example, tert-butoxycarbonyl, benzyl or benzyloxycarbonyl groups may be removed by hydrogenolysis in the presence of a catalyst e.g. palladium; a trichloroethoxycarbonyl group may be removed with zinc dust; and a trityl group may be removed under acidic conditions using standard procedures. Where hydroxyl groups require protection, this may be effected by the formation of esters or trialkylsilyl, tetrahydropyran or benzyl ethers. Such derivatives may be deprotected by standard procedures thus, for example, a tetrahydropyran ether derivative may be deprotected using hydrochloric acid in methanol.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

[$^{18}$F]F$^-$ and [$^{11}$C]CO$_2$ was purchased from PETnet Pharmaceuticals, Inc., North Wales, Pa. The [$^{11}$C]CO$_2$ was converted to [$^{11}$C]MeI using a GE Medical Systems TRACERlab FCX system. The [$^{18}$F]F$^-$ was transported to the radiochemistry lab on an anion exchange resin and eluted prior to use.

EXAMPLE 1

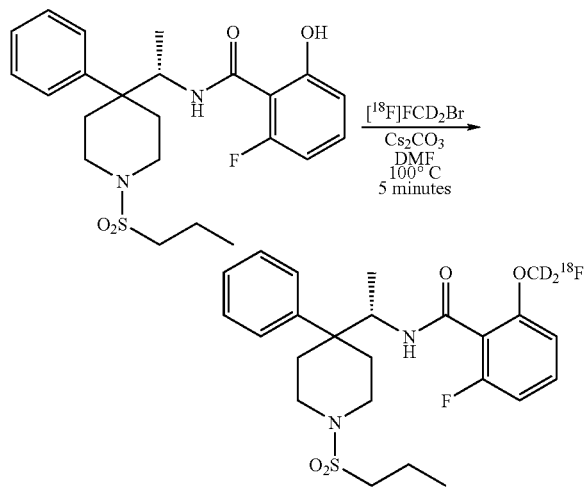

[$^{18}$F] 2-Fluoro-6-fluoromethoxy-N-{[4-phenyl-1-(propylsulfonyl)piperidin-4-yl]ethyl}benzamide-d$_2$ The resin containing the [$^{18}$F]F$^-$ was eluted with 1.5 mL of a solution of 80:20 MeCN:Oxalate solution [0.05 mL of (200 mg K$_2$C$_2$O$_4$/3 mg K$_2$CO$_3$/5 mL H$_2$O)+0.25 mL H$_2$O+1.2 mL MeCN] and transferred to the reaction vessel giving 586 mCi of activity. A solution (0.2 mL) of Kryptofix222 (36 mg/mL MeCN) was added and the mixture was heated to 95° C. under vacuum and argon flow to dryness. Additional aliquots of MeCN (3×0.7 mL) were used to further dry the [$^{18}$F]F$^-$. A solution of CD$_2$Br$_2$ (0.05 mL) in MeCN (1 mL) was added and the mixture was heated at 95° C. Argon flow was used to distill the [$^{18}$F]FCD$_2$Br into a 0° C. mixture of 2-fluoro-6-hydroxy-N-{[4-phenyl-1-(propylsulfonyl)piperidin-4-yl]ethyl}benzamide (0.3 mg) [prepared as described in PCT publication WO2005/046601] in DMF (0.2 mL) containing Cs$_2$CO$_3$ (~1-2 mg). When the amount of trapped activity was sufficient, the mixture was heated at 100° C. for 5 minutes. The reaction was diluted with H$_2$O (0.8 mL) and purified by HPLC (Waters C18 μBondapak, 7.8×300 mm, 10 μm, 3 mL/minute, isocratic for 10 minutes, 50% MeCN:(95:5:0.1) H$_2$O:MeCN:TFA, then 5 minute linear gradient to 95% MeCN, product elutes at ~9 minutes). The product fraction was collected in a heated round bottom flask attached to a rotary evaporator, the solvent was removed and the product was transferred to a vial using physiologic saline to give 15 mCi of [$^{18}$F] 2-fluoro-6-fluoromethoxy-N-{[4-phenyl-1-(propylsulfonyl)-piperidin-4-yl]ethyl}benzamide-d$_2$ Intermediate 2 tert-Butyl 4-cyano-4-pyridin-2-ylpiperidine-1-carboxylate

A solution of 2-fluoropyridine (5.83 g, 60 mmol) and tert-butyl 4-cyanopiperidine-1-carboxylate (I-1, 4.22 g, 20 mmol) in toluene (40 mL) at room temperature was treated with KHMDS (48 mL of a 0.5 M solution, 24 mmol). After stirring 2 h, the reaction mixture was poured into brine (150 mL) and extracted with EtOAc (3×150 mL). The combined organic extracts were washed with brine (2×150 mL), dried (MgSO$_4$), and concentrated under reduced pressure to afford tert-butyl 4-cyano-4-pyridin-2-ylpiperidine-1-carboxylate (I-2) as a yellow-brown solid. Analytical LCMS: single peak (214 nm), 3.076 min. This material was used in subsequent reactions without further purification.

1-(Propylsulfonyl)-4-pyridin-2-ylpiperidine-4-carbonitrile tert-Butyl 4-cyano-4-pyridin-2-ylpiperidine-1-carboxylate (5.45 g, 19 mmol) was dissolved in TFA/CH$_2$Cl$_2$ (1:1, 50 mL) at 0° C. After stirring 40 min, the reaction mixture was concentrated under reduced pressure. The residue was diluted with 2 N NaOH in saturated aqueous NaCl (1:1, 80 mL) and extracted with EtOAc (5×200 mL). The combined extracts were washed with saturated aqueous NaCl, dried (MgSO$_4$), and concentrated under reduced pressure to afford 4-pyridin-2-ylpiperidine-4-carbonitrile (3.55 g, 19 mmol) which was used immediately in subsequent reactions. A solution of 4-pyridin-2-ylpiperidine-4-carbonitrile (3.55 g, 19 mmol) in CH$_2$Cl$_2$ (50 mL) at 0° C. was treated with i-Pr$_2$NEt (10 mL) and n-PrSO$_2$Cl (2.24 mL, 21 mmol). After stirring for 1 h at 0° C., the reaction mixture was treated with 2 N NaOH and stirred vigorously for an additional 1 h, before being extracted with EtOAc (4×200 mL). The combined organic extracts were washed with saturated aqueous NaCl, dried (MgSO$_4$), and concentrated under reduced pressure to afford 1-(propylsulfonyl)-4-pyridin-2-ylpiperidine-4-carbonitrile. This material was used in subsequent reactions without further purification.

{(1S)-1-[1-(Propylsulfonyl)-4-pyridin-2-ylpiperidin-4-yl]ethyl}amine

A solution of 1-(propylsulfonyl)-4-pyridin-2-ylpiperidine-4-carbonitrile (5.0 g, 17 mmol) in toluene (130 mL) at room temperature was treated with MeMgBr (48.9 mL of a 1.0 M solution in dibutyl ether, 28.9 mmol). After 18 h, the reaction was cooled to 0° C. and treated with MeOH (29 mL). After 10 min, the reaction was treated with NaBH$_4$ (1.0 g, 26.4 mmol), warmed to room temperature, and stirred an additional 10 min after which the reaction mixture was cooled to 0° C. and quenched with the dropwise addition of saturated aqueous NH$_4$Cl (15 mL). The reaction was diluted with H$_2$O (300 mL) and extracted with EtOAc (3×200 mL). The combined organic extracts were dried (Na$_2$SO$_4$), concentrated under reduced pressure, and dissolved in pH 7 phosphate buffer (300 mL). The buffered solution was washed with EtOAc (200 mL) and the organic layer was extracted with fresh pH 7 buffer (2×150 mL). The combined buffer solutions were made basic with concentrated NH$_4$OH and extracted with CH$_2$Cl$_2$ (3×200 mL), and these extracts were dried (Na$_2$SO$_4$) and concentrated under reduced pressure to afford {1-[1-(propylsulfonyl)-4-pyridin-2-ylpiperidin-4-yl]ethyl}amine. This material was fully resolved into 1R and 1S isomers (>99% ee) using a ChiralPak AD column. NOE analysis of Mosher's amides and single X-ray crystal analysis of a derivative confirmed the absolute stereochemistry of each isomer.

2,6-Dichloro-N-{(1S)-1-[1-(propylsulfonyl)-4-pyridin-2-ylpiperidin-4-yl]ethyl}benzamide A solution of {(1S)-1-[1-(propylsulfonyl)-4-pyridin-2-ylpiperidin-4-yl]ethyl}amine (80 mg, 0.26 mmol) in DMF (0.7 mL) was treated with i-Pr2NEt (0.2 mL, 1.15 mmol) and 2,6-dichloro-benzoyl chloride (0.15 mL, 0.8 mmol) and stirred at room temperature for 30 min. The reaction mixture was purified directly by reverse phase HPLC to afford the desired product.

EXAMPLE 2

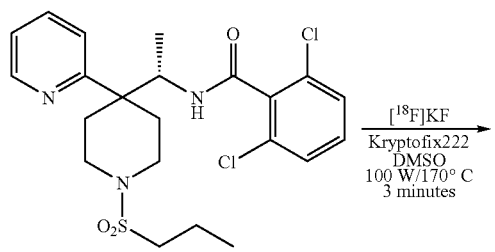

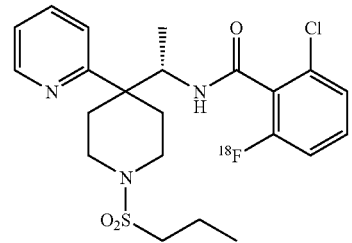

[$^{18}$F]2-Chloro-6-fluoro-N-{[1-(propylsulfonyl)-4-pyridin-2-ylpiperidin-4-yl]ethyl}benzamide The [$^{18}$F]F$^-$ containing anion exchange resin was eluted with a mixture (1 mL) of 80% MeCN:20% oxalate*(aq.) solution [*0.05 mL of (200 mg K$_2$C$_2$O$_4$/3 mg K$_2$CO$_3$/5 mL H$_2$O)+0.25 mL H$_2$O+1.2 mL MeCN] and added to a 1 mL v-vial in the microwave cavity. This vial was vented using an 18G1 syringe needle attached to a gas bag. To the aqueous fluoride solution (51 mCi) was added Kryptofix222 (0.2 mL, 36 mg/mL MeCN) and the fluoride was dried under argon flow in the microwave (35 W, 65° C.). Additional aliquots of acetonitrile (3×0.5 mL) were added for azeotropic drying. A solution of 2,6-dichloro-N-{[1-(propylsulfonyl)-4-pyridin-2-ylpiperidin-4-yl]ethyl}benzamide (1.1 mg) in DMSO (0.2 mL) was added to the microwave vial, the vent line was removed, and the reaction mixture was heated at 100 W, 150° C. for 4 minutes. After cooling to <60° C., the reaction was diluted with H$_2$O (0.8 mL) and purified by HPLC (Waters C18 XTerra, 7.8×150 mm, 7 μm, 15 minutes linear gradient 20% MeCN:(95:5:0.1) H$_2$O:MeCN:TFA to 90% MeCN @ 3 mL/min, product elutes at 6.5 minutes). The product fraction was collected in a heated round bottom flask attached to a rotary evaporator, the solvent was removed and the product was transferred to a vial using physiologic saline to give to give 1.2 mCi of [$^{18}$F]2-chloro-6-fluoro-N-{[1-(propylsulfonyl)-4-pyridin-2-ylpiperidin-4-yl]ethyl}benzamide.

Intermediate 3

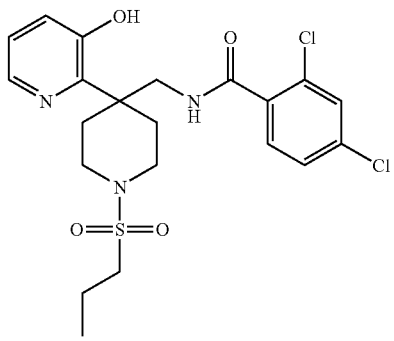

2,4-Dichloro-N-{[4-(3-hydroxypyridin-2-yl)-1-(propylsulfonyl)piperidin-4-yl]methyl}benzamide tert-Butyl 4-cyano-4-[3-(methoxymethoxy)pyridin-2-yl]piperidine-1-carboxylate 2-Chloro-3-methoxymethoxy-pyridine (Tetrahedron 58 (2002), 309-314) (2 g, 11.5 mmol) and tert-butyl 4-cyanopiperidine-1-carboxylate (1.6 g, 7.7 mmol) were reacted in the presence of potassium hexamethyldisilazide (9.2 mmol) using the method in example 8-1 to afford the desired product: tert-Butyl 4-cyano-4-[3-(methoxymethoxy)pyridin-2-yl]piperidine-1-carboxylate: 1H NMR δ (ppm) (CDCl3): 8.21 (1H, d, J=4.6 Hz), 7.53 (1H, d, J=8.3 Hz), 7.27-7.23 (1H, m), 5.31 (2H, s), 4.20 (2H, br s), 3.55 (3H, s), 3.28 (2H, br s), 2.35 (2H, s), 2.10 (2H, br s), 1.47 (9H, s).

tert-Butyl 4-{[(2,4-dichlorobenzoyl)amino]methyl}-4-[3-(methoxymethoxy)pyridin-2-yl]piperidine-1-carboxylate tert-Butyl 4-cyano-4-[3-(methoxymethoxy)pyridin-2-yl]piperidine-1-carboxylate was reduced using Raney nickel and acylated using 2,4-dichlorobenzoyl chloride using the method exemplified in example 8-1 to afford the desired product: tert-butyl 4-{[(2,4-dichlorobenzoyl)amino]-methyl}-4-[3-(methoxymethoxy)pyridin-2-yl]piperidine-1-carboxylate: 1H NMR δ (ppm) (CDCl3): 8.18 (1H, dd, J=1.3, 4.5 Hz), 7.50-7.46 (2H, m), 7.33 (1H, d, J=1.9 Hz), 7.25 (1H, dd, J=8.3, 2.0), 7.15 (1H, dd, J=4.6, 8.3 Hz), 6.70 (1H, m), 5.25 (2H, s), 4.01 (2H, br s), 3.68-3.62 (2H, m), 3.49 (3H, s), 3.44-3.38 (2H, m), 2.75-2.69 (2H, m), 1.66-1.60 (1H, m) 1.46 (9H, s).

2,4-Dichloro-N-{[4-(3-hydroxypyridin-2-yl)-1-(propylsulfonyl)piperidin-4-yl]methyl}benzamide A solution of tert-butyl 4-{[(2,4-dichlorobenzoyl)amino]methyl}-4-[3-methoxypyridin-2-yl]piperidine-1-carboxylate (200 mg, 0.38 mmol) was formed in methanol (5 mL). Hydrochloric acid (conc., 2 mL) was added and the mixture stirred for 24 hours at room temperature. The solvent was removed under vacuum and the residue was dissolved in dichloromethane (5 mL) with N,N-diisopropylethylamine (0.26 mL, 1.5 mmol). 1-Propanesulphonyl chloride (89 μL, 0.8 mmol) was added and the mixture stirred at room temperature for 2 hours. The solvent was removed under vacuum and the residue was re-dissolved in methanol (5 mL) and aqueous sodium hydroxide (1 mL, 4 N) was added. The mixture was heated at reflux for 20 minutes then allowed to cool and poured into water (20 mL) and extracted with ethyl acetate (3×20 mL). The combined organic phases were dried over magnesium sulphate (anhydrous), filtered and evaporated. The reside was purified by flash column chromatography on silica gel using a 40% ethyl acetate: 60% dichloromethane mixture as eluent to afford the desired product: 2,4-dichloro-N-{[4-(3-hydroxypyridin-2-yl)-1-(propylsulfonyl)piperidin-4-yl]methyl}benzamide: 1H NMR δ (ppm) (CDCl3): 8.09 (1H, dd, J=1.3, 4.5 Hz), 7.47 (1H, s), 7.44 (1H, d, J=8.3 Hz), 7.35 (1H, d, J=1.9 Hz), 7.26 (1H, dd, J=8.3, 1.9), 7.16 (1H, dd, J=1.2, 8.1 Hz), 7.07 (1H, dd, J=4.6, 8.0 Hz), 6.95 (1H, t, J=5.8 Hz), 4.00 (2H, d, J=6.1 Hz), 3.56-3.50 (2H, m), 3.27-3.23 (2H, m), 2.99-2.97 (2H, m), 2.86-2.84 (2H, m), 1.85-1.78 (2H, m), 1.73-1.67 (2H, m), 1.03 (3H, t, J=7.4 Hz); m/z (ES) 486, (M+H).

EXAMPLE 3

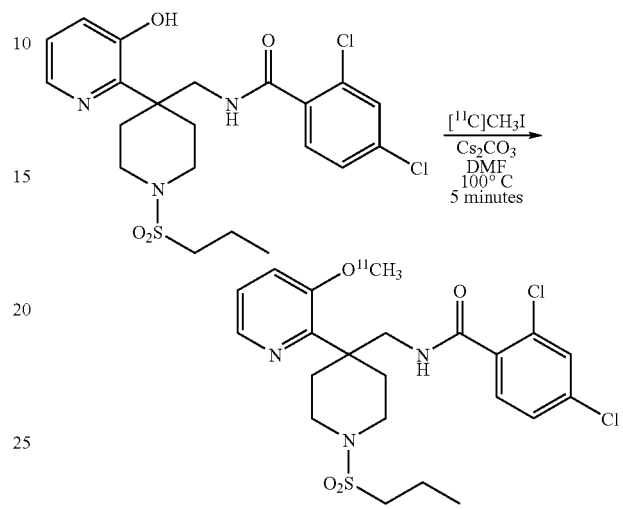

[$^{11}$C] 2,4-Dichloro-N-{[4-(3-methoxypyridin-2-yl)-1-(propylsulfonyl)piperidin 4-yl]methyl}benzamide The [$^{11}$C]MeI was trapped at 0° C. in a mixture of 2,4-dichloro-N-{[4-(3-hydroxypyridin-2-yl)-1-(propylsulfonyl)piperidin-4-yl]methyl}benzamide (0.25 mg) in DMF (0.2 mL) containing Cs$_2$CO$_3$ (1-2 mg). This mixture was transferred to a vial at 100° C. and heated for five minutes. The reaction was diluted with H$_2$O (0.8 μL) and purified by HPLC (Waters C18 XTerra, 7.8×150 mm, 5 μm, 15 minutes linear gradient 20% MeCN:(95:5:0.1) H$_2$O:MeCN:TFA to 90% MeCN @ 3 mL/min, product elutes at 8.5 minutes). The product fraction was collected in a heated round bottom flask attached to a rotary evaporator, the solvent was removed and the product was transferred to a vial using physiologic saline to give to give 65 mCi of [$^{11}$C] 2,4-dichloro-N-{[4-(3-methoxypyridin-2-yl)-1-(propylsulfonyl)piperidin-4-yl]methyl}benzamide.

Intermediate 4

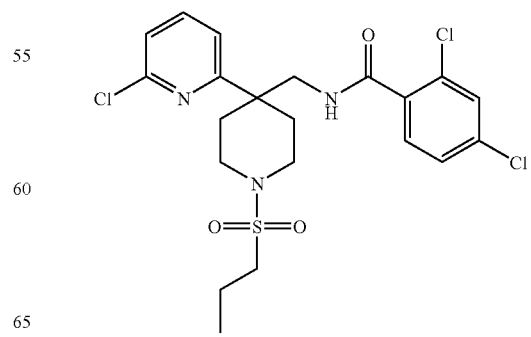

2,4-Dichloro-N-{[4-(6-chloropyridin-2-yl)-1-(propylsulfonyl)piperidin-4-yl]methyl}benzamide tert-Butyl 4-cyano-4-(6-chloropyridin-2-yl)piperidine-1-carboxylate

A solution of tert-butyl 4-cyanopiperidine-1-carboxylate (6.3 g, 30 mmol) and 2,6-dichloropyridine (5 g, 45 mmol) was formed in toluene (50 mL) and cool in an ice-bath while potassium hexamethyldisilazide (72 mL, 0.5 M in toluene) was added dropwise. The mixture was then allowed to warm to room temperature over night. The solution was poured into water (200 mL) and extracted with ethyl acetate (3×200 mL). The combined organic phases were dried over magnesium sulphate (anhydrous), filtered and evaporated to an orange oil. Purification by flash column chromatography on silica gel using dichloromethane containing 5% ethyl acetate as eluent afforded the desired product.

tert-Butyl 4-(aminomethyl)-4-(6-chloropyridin-2-yl)piperidine-1-carboxylate A solution of tert-butyl 4-cyano-4-(6-chloropyridin-2-yl)piperidine-1-carboxylate (0.82 mmol) in methanol (20 mL) with triethylamine (1 mL) was reacted with Raney nickel (0.5 mL of 50% slurry in water) under 40 psi hydrogen for 5 hours. The catalyst was filtered off and washed thoroughly with methanol. Evaporation of the solvent afforded the desired product.

tert-Butyl 4-{[(2,4-dichlorobenzoyl)amino]methyl}-4-(6-chloropyridin-2-yl)piperidine-1-carboxylate A solution of tert-Butyl 4-(aminomethyl)-4-(6-chloropyridin-2-yl)piperidine-1-carboxylate (0.82 mmol) and N,N-diisopropylethylamine (0.88 mmol) was formed in dichloromethane (10 mL). 2,4-Dichlorobenzoyl chloride (0.12 mL, 0.82 mmol) was added dropwise and the mixture stirred at room temperature for 2 hours. The mixture was poured into water (20 mL) and extracted with dichloromethane (3×20 mL). The combined organic phases were dried over magnesium sulphate (anhydrous), filtered and evaporated to an orange oil. Purification by flash column chromatography on silica gel using dichloromethane containing 10% ethyl acetate as eluent afforded the desired product.

2,4-Dichloro-N-{[4-(6-chloropyridin-2-yl)-1-(propylsulfonyl)piperidin-4-yl]methyl}benzamide A solution of tert-butyl 4-{[(2,4-dichlorobenzoyl)amino]methyl}-4-(6-chloropyridin-2-yl)piperidine-1-carboxylate (0.7 mmol) was formed in dichloromethane (3 mL). Trifluoroacetic acid (1 mL) was added and the mixture stirred at room temperature for 4 hours. The mixture was poured into aqueous sodium carbonate (20 mL, 2 M) and extracted with dichloromethane (10 mL×2). The combined organic phases were dried over magnesium sulphate (anhydrous), filtered and evaporated to an oil. This was then re-dissolved in dichloromethane (5 mL) and N,N-diisopropylethylamine (0.24 mL, 1.4 mmol) followed by 1-propanesulphonyl chloride (80 μL, 0.7 mmol) were added and the mixture stirred at room temperature over night. The solvent was removed under reduced pressure and the reside purified by flash column chromatography on silica gel using dichloromethane containing 20% ethyl acetate as eluent to afford the desired product: 2,4-dichloro-N-{[4-(6-chloropyridin-2-yl)-1-(propylsulfonyl)piperidin-4-yl]methyl}benzamide: 1H NMR δ (ppm) (CDCl3): 7.69 (1H, t, J=7.8 Hz), 7.63 (1H, d, J=8.3 Hz), 7.40 (1H, d, J=1.9 Hz), 7.32-7.30 (2H, m), 7.24 (1H, d, J=7.8 Hz), 6.94 (1H, m), 3.89 (2H, d, J=6.2 Hz), 3.48-3.40 (4H, m), 2.91-2.89 (2H, m), 2.29-2.23 (2H, m), 1.99-1.95 (2H, m), 1.88-1.81 (2H, m), 1.06 (3H, t, J=7.4 Hz), m/z (ES) 504, 506 (M+H).

EXAMPLE 4

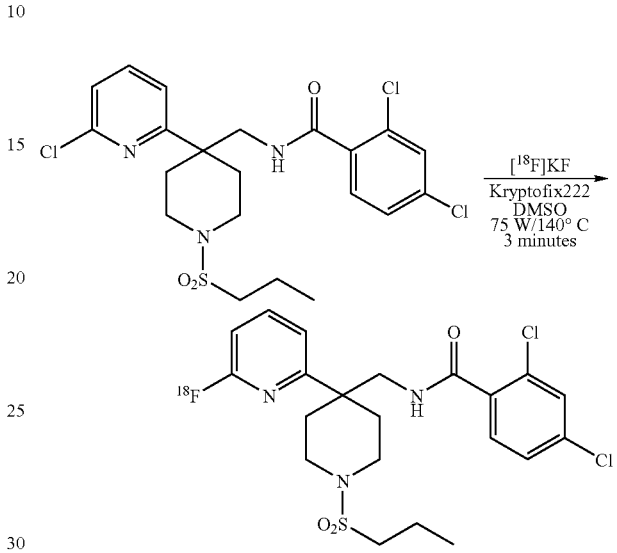

[$^{18}$F] 2,4-Dichloro-N-{[4-(6-fluoropyridin-2-yl)-1-(propylsulfonyl)piperidin-4-yl]methyl}benzamide The [$^{18}$F]F$^-$ containing anion exchange resin was eluted with a mixture (1 mL) of 80% MeCN:20% oxalate*(aq.) solution [*0.05 mL of (200 mg K$_2$C$_2$O$_4$/3 mg K$_2$CO$_3$/5 mL H$_2$O)+0.25 mL H$_2$O+1.2 mL MeCN] and added to a 1 mL v-vial in the microwave cavity. This vial was vented using an 18G1 syringe needle attached to a gas bag. To the aqueous fluoride solution was added Kryptofix222 (0.2 mL, 36 mg/mL MeCN) and the fluoride was dried under argon flow in the microwave (35 W, 65° C.). Additional aliquots of acetonitrile (3×0.5 mL) were added for azeotropic drying. A solution of 2,4-dichloro-N-{[4-(6-chloropyridin-2-yl)-1-(propylsulfonyl)piperidin-4-yl]methyl}benzamide (1.2 mg) in DMSO (0.2 mL) was added to the microwave vial, the vent line was removed, and the reaction mixture was heated at 75 W, 140° C. for 3 minutes. After cooling to <60° C., the reaction was diluted with H$_2$O (0.8 mL) and purified by HPLC (Waters C18 μBondapak, 7.8×300 mm, 10 μm, 3 mL/minute, 20 minute linear gradient, 20% MeCN:(95:5:0.1) H$_2$O:MeCN:TFA to 90% MeCN, product elutes at ~16 minutes. The product fraction was collected in a heated round bottom flask attached to a rotary evaporator, the solvent was removed and the product was transferred to a vial using physiologic saline to give to give 46 mCi of [$^{18}$F] 2,4-dichloro-N-{[4-(6-fluoropyridin-2-yl)-1-(propylsulfonyl)piperidin-4-yl]methyl}-benzamide.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula:

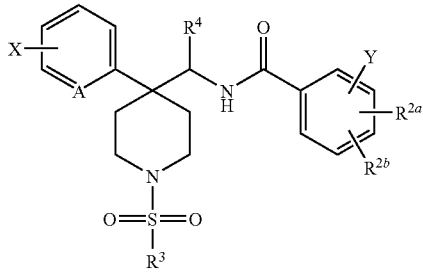

wherein:
  A is selected from N and CH;
  $R^{2a}$ and $R^{2b}$ are independently selected from the group consisting of:
   (1) hydrogen,
   (2) fluoro,
   (3) chloro, and
   (4) bromo;
  $R^3$ is $C_{1-6}$alkyl, which is unsubstituted or substituted with fluoro;
  $R^4$ is selected from the group consisting of:
   (1) hydrogen, and
   (2) $C_{1-3}$alkyl;
  one of X and Y is selected from the group consisting of:
   (1) $^{18}F$,
   (2) $—O(^{11}CH_3)$, and
   (3) $—O(CD_2{}^{18}F)$,
   and the other of X and Y is hydrogen;
or a pharmaceutically acceptable salt thereof or an individual enantiomer or diastereomer thereof.

2. The compound of claim 1 of the formula Ia:

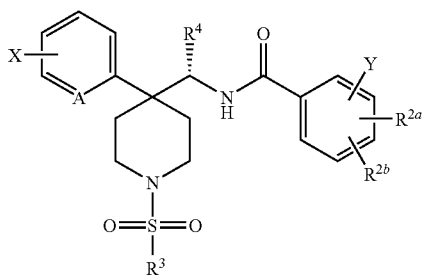

wherein $R^4$ is $C_{1-3}$alkyl;
or a pharmaceutically acceptable salt thereof.

3. The compound of claim 1 of the formula Ib:

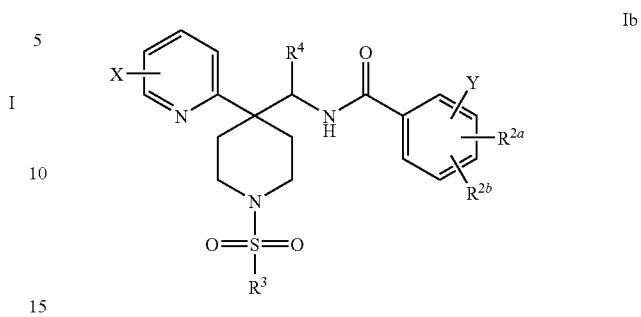

or a pharmaceutically acceptable salt thereof.

4. The compound of claim 1 wherein $R^{2a}$ and $R^{2b}$ are independently selected from the group consisting of:
  (1) hydrogen,
  (2) fluoro, and
  (3) chloro.

5. The compound of claim 4 wherein $R^{2a}$ is chloro and $R^{2b}$ is chloro.

6. The compound of claim 4 wherein $R^{2a}$ is chloro and $R^{2b}$ is hydrogen.

7. The compound of claim 4 wherein $R^{2a}$ is fluoro and $R^{2b}$ is hydrogen.

8. The compound of claim 1 wherein $R^3$ is $—CH_2CH_3$.

9. The compound of claim 1 wherein X is $^{18}F$ and Y is hydrogen.

10. The compound of claim 1 wherein X is hydrogen and Y is $^{18}F$.

11. The compound of claim 1 wherein X is $—O(^{11}CH_3)$ and Y is hydrogen.

12. The compound of claim 1 wherein X is hydrogen and Y is $—O(CD_2{}^{18}F)$.

13. A compound which is selected from the group consisting of:

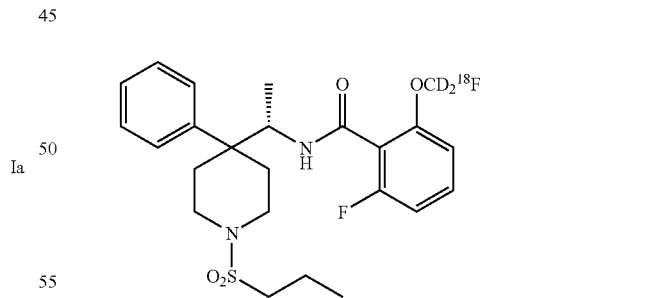

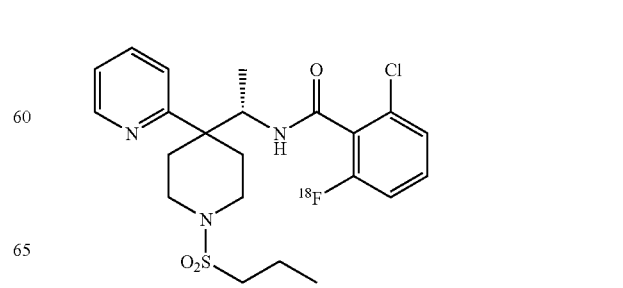

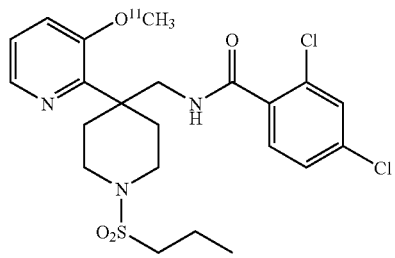
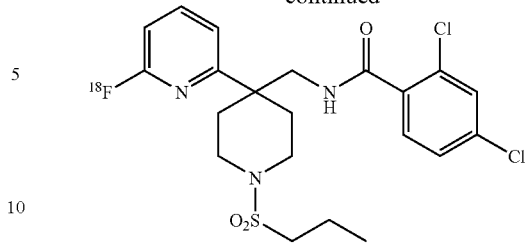
or a pharmaceutically acceptable salt thereof.
14. A radiopharmaceutical composition which comprises the compound of claim 1 and a pharmaceutically acceptable carrier or excipient.
* * * * *